(12) United States Patent
Coggan et al.

(10) Patent No.: US 7,332,630 B2
(45) Date of Patent: Feb. 19, 2008

(54) ARYLAMINE PROCESSES

(75) Inventors: Jennifer A. Coggan, Cambridge (CA); Timothy P. Bender, Toronto (CA)

(73) Assignee: Xerox Corporation, Norwalk, CT (US)

( * ) Notice: Subject to any disclaimer, the term of this patent is extended or adjusted under 35 U.S.C. 154(b) by 196 days.

(21) Appl. No.: 11/274,506

(22) Filed: Nov. 16, 2005

(65) Prior Publication Data

US 2007/0111120 A1    May 17, 2007

(51) Int. Cl.
*C07C 209/10*    (2006.01)
(52) U.S. Cl. .................. 564/405; 564/307; 564/406
(58) Field of Classification Search ............... None
See application file for complete search history.

(56) References Cited

U.S. PATENT DOCUMENTS

| | | | |
|---|---|---|---|
| 4,265,990 A | 5/1981 | Stolka et al. | |
| 5,827,602 A | 10/1998 | Koch et al. | |
| 6,242,648 B1 * | 6/2001 | Yamasaki et al. | 564/405 |
| 6,730,448 B2 | 5/2004 | Yoshino et al. | |
| 2004/0086794 A1 | 5/2004 | Yamada et al. | |

OTHER PUBLICATIONS

Sukata et al., J. Org. Chem. (1989), 54(6), p. 1476-1479.*
U.S. Appl. No. 10/992,690, filed Nov. 22, 2004, Timothy P. Bender et al.
U.S. Appl. No. 10/992,687, filed Nov. 22, 2004, Timothy P. Bender et al.
U.S. Appl. No. 10/992,658, filed Nov. 22, 2004, H. Bruce Goodbrand et al.
U.S. Appl. No. 11/094,683, filed Mar. 31, 2005, H. Bruce Goodbrand et al.
U.S. Appl. No. 10/998,585, filed Nov. 30, 2004, Timothy P. Bender et al.
U.S. Appl. No. 11/034,713, filed Jan. 14, 2005, Yu Qi et al.
U.S. Appl. No. 10/709,193, filed Apr. 20, 2004, H. Bruce Goodbrand et al.
U.S. Appl. No. 11/263,671, filed Nov. 1, 2005, Timothy P. Bender et al.
Michele C. Harris et al; "One-Pot Synthesis of Unsymmetrical Triarylamines from Aniline Precursors"; *J. Org. Chem.* 65, pp. 5327-5333 (2000).
James McNulty et al., "Suzuki cross-coupling reactions of aryl halides in phosphonium salt ionic liquid under mild conditions," *Chem. Commun.*, pp. 1986-1987 (2002).
David A. Gerritsma et al., "Heck reactions of aryl halides in phosphonium salt ionic liquids: library screening and Applications," *Tetrahedron Letters*, 45(41), pp. 7629-7631 (2004).
Jin-Heng Li et al., "Recyclable and Reusable $Pd(OAc)_2$/DABCO/PEG-400 System for Suzuki-Miyaura-Coupling Reaction," *Organic Letters*, vol. 4, No. 25, pp. 4399-4401 (2002).
S. Chandrasekhar et al., "Polyethylene glycol (PEG) as a Reusable Solvent Medium for Organic Synthesis, Application in the Heck Reaction," *Journal of Organic Chemistry*, vol. 70, pp. 5409-5412 (2005).

* cited by examiner

*Primary Examiner*—Brian Davis
(74) *Attorney, Agent, or Firm*—Oliff & Berridge, PLC (57) ABSTRACT

A process for the preparation of a tertiary arylamine compound, comprising reacting an arylhalide, such as an arylbromide, and an arylamine in an alkylene glycol compound in the presence of a catalyst.

27 Claims, 4 Drawing Sheets

ARYLAMINE PROCESSES

TECHNICAL FIELD

This disclosure is generally directed to processes for the synthesis of arylamine compounds, and to the use of such compounds in electrophotographic imaging members. In particular, this disclosure provides processes for the preparation of arylamine molecules by the reaction of an arylhalide such as an arylbromide with an arylamine in an alkylene glycol compound such as a polyethylene glycol compound as a solvent or a co-solvent and using a catalyst such as a palladium catalyst, and where the palladium catalyst can be recycled.

RELATED APPLICATIONS

Commonly assigned, U.S. patent application Ser. No. 10/992,690 filed Nov. 22, 2004, describes a process for forming a tertiary arylamine compound, comprising reacting an arylbromide and an arylamine. For example, the application describes a process for forming N,N-diphenyl-4-aminobiphenyl, comprising reacting 4-bromobiphenyl and diphenylamine in the presence of a palladium ligated catalyst.

Commonly assigned, U.S. patent application Ser. No. 11/263,671 filed Nov. 1, 2005, entitled "Arylamine Processes", describes a process for the preparation of a tertiary arylamine compound, comprising reacting an arylhalide and an arylamine in an ionic liquid in the presence of a catalyst. For example, the application describes a process for forming N,N-diphenyl-aminobiphenyl such as N,N-diphenyl-4-aminobiphenyl, comprising reacting bromobiphenyl such as 4-bromobiphenyl and diphenylamine in an ionic liquid in the presence of a palladium catalyst. The processes allow the palladium catalyst to be recycled.

Commonly assigned, U.S. patent application Ser. No. 10/992,687 filed Nov. 22, 2004, describes a process for forming a 4-aminobiphenyl derivative arylamine compound, comprising: (i) providing a first disubstituted 4-aminobiphenyl compound; (ii) optionally formylating the first disubstituted 4-aminobiphenyl compound to form a bisformyl substituted compound, where the first disubstituted 4-aminobiphenyl compound is not a bisformyl substituted compound; (iii) acidifying the bisformyl substituted compound to convert formyl functional groups into acid functional groups to form an acidified compound; and (iv) hydrogenating the acidified compound to saturate at least one unsaturated double bonds in the acidified compound, wherein there is provided a second disubstituted 4-aminobiphenyl compound.

Commonly assigned, U.S. patent application Ser. No. 10/992,658 filed Nov. 22, 2004, describes a process for forming a 4-aminobiphenyl derivative arylamine compound, comprising: (i) providing an iodinated organic compound; (ii) substituting the iodinated organic compound at carboxylic acid groups thereof to provide ester protecting groups; (iii) conducting an Ullman condensation reaction to convert the product of step (ii) into an arylamine compound; and (iv) conducting a Suzuki coupling reaction to add an additional phenyl group to the arylamine compound in the 4-position relative to the nitrogen, to provide the 4-aminobiphenyl derivative arylamine compound.

Commonly assigned, U.S. patent application Ser. No. 11/094,683 filed Mar. 31, 2005, describes a process for forming an anhydrous alkali earth salt of a dicarboxylic acid of an arylamine compound, comprising reacting a dicarboxylic acid of an arylamine compound with an anhydrous alkali earth salt. The application also discloses a process for forming a siloxane-containing hole transport molecule, comprising: reacting a dicarboxylic acid of an arylamine compound with an anhydrous alkali earth salt to form an anhydrous dicarboxylic acid salt of the arylamine compound; and reacting the anhydrous dicarboxylic acid salt of the arylamine compound with a siloxane-containing compound.

Commonly assigned, U.S. patent application Ser. No. 10/998,585 filed Nov. 30, 2004, describes a silicon-containing layer for electrophotographic photoreceptors comprising: one or more siloxane-containing compound; and one or more siloxane-containing antioxidant; wherein the siloxane-containing antioxidant is at least one member selected from the group consisting of hindered phenol antioxidants, hindered amine antioxidants, thioether antioxidants and phosphite antioxidants.

Commonly assigned, U.S. patent application Ser. No. 11/034,713 filed Jan. 14, 2005, describes an electrophotographic photoreceptor comprising a charge generating layer, a charge transport layer, and an overcoat layer comprised of a crosslinked siloxane composite composition comprising at least one siloxane-containing compound and metal oxide particles.

Commonly assigned, U.S. patent application Ser. No. 10/709,193 filed Apr. 20, 2004, describes a process for preparing an aryl iodide compound, comprising: reacting an aryl halide compound with a metal iodide, a metal catalyst and a catalyst coordinating ligand in at least one solvent to form an aryl iodide; and purifying the aryl iodide; wherein the solvent is heated to reflux during the reacting; wherein an aryl iodide yield of at least about 75% is obtained; and wherein the aryl iodide has a purity of at least 90%.

The appropriate components and process aspects of each of the foregoing, such as the arylamine precursor and catalyst materials and electrophotographic imaging members, may be selected for the present disclosure in embodiments thereof. The entire disclosures of the above-mentioned applications are totally incorporated herein by reference.

REFERENCES

Buchwald et al. (MIT) and Hartwig et al. (Yale) have both reported over the past several years on the general versatility of palladium based catalysts for the formation of nitrogen-carbon bonds. While their work has focused on the arylation of alkylamine and alkylamides, they have reported the use of a palladium based catalyst for arylamine synthesis starting from an arylbromide or an arylchloride. See Michele C. HARRIS et al; "One-Pot Synthesis of Unsymmetrical Tri-arylamines from Aniline Precursors"; *J. Org. Chem.* Vol. 65, pp. 5327-5333 (2000). The present disclosure adapts the procedure for the production of arylamine derivatives, specifically arylamine derivatives of 4-aminobiphenyl. More specifically, this disclosure pertains to the use of ligated palladium catalyzed production of arylamine derivatives (for example derivatives of 4-aminobiphenyl) by reaction of an arylamine (for example diphenylamine) with an arylbromide (for example 4-bromobiphenyl) in the presence of a base (for example sodium tert-butoxide) in a short period of time, in an economical way and isolatable in suitable purity as to be used as starting materials for the further synthesis of arylamine derivatives, for example, for application in electrophotographic photoreceptors or organic light emitting diodes, or alternatively itself could be suitable for application in electrophotographic photoreceptors, organic light emitting diodes, and the like.

The disclosures of each of the foregoing patents and publications are hereby incorporated by reference herein in their entireties. The appropriate components and process aspects of the each of the foregoing patents and publications may also be selected for the present compositions and processes in embodiments thereof.

BACKGROUND

In electrophotography, an electrophotographic substrate containing a photoconductive insulating layer on a conductive layer is imaged by first uniformly electrostatically charging a surface of the substrate. The substrate is then exposed to a pattern of activating electromagnetic radiation, such as, for example, light. The light or other electromagnetic radiation selectively dissipates the charge in illuminated areas of the photoconductive insulating layer while leaving behind an electrostatic latent image in non-illuminated areas of the photoconductive insulating layer. This electrostatic latent image is then developed to form a visible image by depositing finely divided electroscopic marking particles on the surface of the photoconductive insulating layer. The resulting visible image is then transferred from the electrophotographic substrate to a necessary member, such as, for example, an intermediate transfer member or a print substrate, such as paper. This image developing process can be repeated as many times as necessary with reusable photoconductive insulating layers.

In image forming apparatus such as copiers, printers and facsimiles, electrophotographic systems in which charging, exposure, development, transfer, etc. are carried out using electrophotographic photoreceptors have been widely employed. In such image forming apparatus, demands for speeding up of image formation processes, improvement in image quality, miniaturization and prolonged life of the apparatus, reduction in production cost and running cost, etc. are increasingly growing. Further, with recent advances in computers and communication technology, digital systems and color image output systems have been applied also to the image forming apparatus.

Electrophotographic imaging members (i.e. photoreceptors) are known. Electrophotographic imaging members are commonly used in electrophotographic processes having either a flexible belt or a rigid drum configuration. These electrophotographic imaging members sometimes comprise a photoconductive layer including a single layer or composite layers. These electrophotographic imaging members take many different forms. For example, layered photoresponsive imaging members are known in the art. U.S. Pat. No. 4,265,990 to Stolka et al., which is totally incorporated herein by reference, describes a layered photoreceptor having separate photogenerating and charge transport layers. The photogenerating layer disclosed in the 990 patent is capable of photogenerating holes and injecting the photogenerated holes into the charge transport layer. Thus, in the photoreceptors of the 990 patent, the photogenerating material generates electrons and holes when subjected to light.

More advanced photoconductive photoreceptors containing highly specialized component layers are also known. For example, a multilayered photoreceptor employed in electrophotographic imaging systems sometimes includes one or more of a substrate, an undercoating layer, an intermediate layer, an optional hole or charge blocking layer, a charge generating layer (including a photogenerating material in a binder) over an undercoating layer and/or a blocking layer, and a charge transport layer (including a charge transport material in a binder). Additional layers such as one or more overcoat layer or layers are also sometimes included.

In view of such a background, improvement in electrophotographic properties and durability, miniaturization, reduction in cost, etc., in electrophotographic photoreceptors have been studied, and electrophotographic photoreceptors using various materials have been proposed.

SUMMARY

The present disclosure addresses these and other needs, by providing a method for the production of an arylamine molecule in an alkylene glycol compound as a solvent or a co-solvent using a suitable catalyst such as a palladium catalyst, where the palladium catalyst can be recycled. In embodiments, the disclosure provides methods for forming derivatives of compounds (such as substituted compounds), without requiring use of the basic compound itself, which may be hard to obtain or may pose environmental or health dangers. For example, the disclosure provides a process for forming an arylamine molecule that is a derivative to 4-aminobiphenyl, but the process allows its production without the use of 4-aminobiphenyl compound itself from readily available commercial materials. Generally, for the formation of derivatives of 4-aminobiphenyl, the compound 4-aminobiphenyl is itself used as a starting or raw material. However, because 4-aminobiphenyl is a known human carcinogen, its use in a manufacturing/industrial setting is not desirable.

The above problem has been overcome by derivatization of a diarylamine molecule (for example diphenylamine) with 4-iodobiphenyl under traditional Ullman condensation conditions. As 4-iodobiphenyl is not a commercially available material, its synthesis from biphenyl by iodoination is necessary. However, iodination of biphenyl is known to produce amounts of diiodobiphenyl and leave a residue of biphenyl in its reaction products, each of which is removed for the iodobiphenyl to be of practical use. This separation and purification of 4-iodobiphenyl is time consuming and costly, resulting in the product being an estimated 10 fold more expensive than 4-bromobiphenyl. In contrast, 4-bromobiphenyl is commercially available in purities suitable for use as a feedstock in arylamine production; however, its reactivity under standard Ullman conditions is not facile enough to allow for reaction in an economical amount of time. Therefore there is a need for a process by which 4-bromobiphenyl can be used as a feedstock for the production of arylamine derivatives, specifically arylamine derivatives of 4-aminobiphenyl.

In commonly assigned U.S. patent application Ser. No. 10/992,690 filed Nov. 22, 2004, described above, 4-bromobiphenyl is used as a feedstock for the production of arylamine derivatives by reacting 4-bromobiphenyl and diphenylamine in the presence of a palladium ligated catalyst. However, the palladium catalyst is expensive, and it is desired to improve the process by allowing the catalyst to be more easily recycled for future use.

To offset the high cost of the palladium catalyst, further improvements are desired that would allow the palladium catalyst to be recycled for use in multiple reaction cycles. One such recycling method is provided herein.

These and other features and advantages of various exemplary embodiments of materials, devices, systems and/or methods according to this disclosure are described in, or are apparent from, the following detailed description of the various exemplary embodiments of the methods and systems according to this disclosure.

In an embodiment, the present disclosure provides a process for forming a tertiary arylamine compound, comprising reacting an arylhalide such as an arylbromide and an arylamine in an alkylene glycol compound as a solvent or a co-solvent in the presence of a catalyst, to form a reaction product. For example, the disclosure provides a process for forming N,N-diphenyl-4-aminobiphenyl, comprising reacting 4-bromobiphenyl and diphenylamine in a polyethylene glycol compound as a solvent or a co-solvent in the presence of a palladium catalyst.

Figure 5:
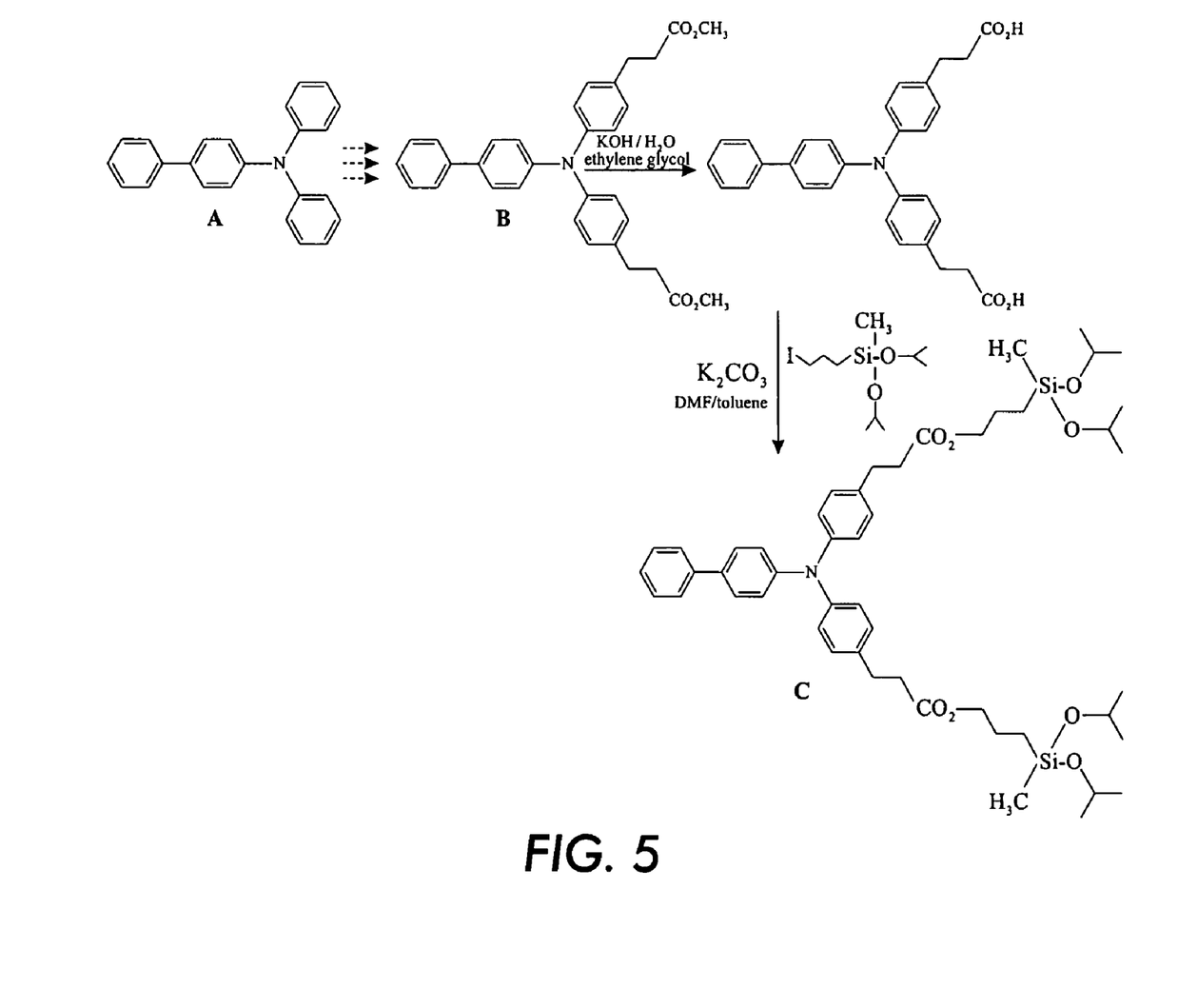
FIG. 5 sets forth a process by which a siloxane containing arylamine can be produced.

In the case where the arylamine is used as a starting material for the further derivatization of arylamine molecules, it can be used to synthesize a compound containing siloxane groups (see, for example. Compound C in FIG. 5). Such siloxane group containing compounds are useful, for example, in the preparation of siloxane containing charge transporting layers or overcoating layers for electrophotographic application.

In another embodiment, the present disclosure provides a process for forming a tertiary arylamine compound, comprising:
(a) forming a reaction medium comprising an arylbromide, an arylamine, an alkylene glycol compound, and a catalyst;
(b) allowing the arylbromide and the arylamine to react in the reaction medium to form a reaction product;
(c) adding an organic solvent to the reaction product to form a multi-phase system comprising a first phase comprising the tertiary arylamine and the organic solvent, and a second phase comprising the catalyst and the alkylene glycol compound;
(d) separating the first phase from the second phase;
(e) adding additional arylbromide and arylamine to the second phase to form an additional reaction medium; and
(f) repeating (b) to (d) at least one additional time to form additional arylamine compounds.

EMBODIMENTS

Production of a number of arylamine compounds, such as arylamine compounds that are useful as charge transport compounds in electrostatographic imaging devices and processes, often involves synthesis of intermediate materials, some of which generally are costly and/or time-consuming to produce, and some of which involve a multi-step process. One such intermediate product is the arylamine N,N-diphenyl-4-aminobiphenyl, which is useful as a charge transport compound in electrostatographic imaging devices and processes. Even production of this intermediate compound currently involves a long, costly process.

For example, N,N-diphenyl-4-aminobiphenyl has been produced by reacting 4-iodobiphenyl and diphenylamine under standard Ullman condensation conditions. However, 4-iodobiphenyl is an expensive material and is not readily available in many countries, such as the United States. While the process for producing 4-iodobiphenyl is known, it is costly and time consuming and especially time consuming to purify to a level suitable for further reaction and processes. Alternatively, the process could be conducted using 4-bromobiphenyl, which is more readily available and is 10-fold cheaper. However, the rate of reaction of arylbromides is known to be significantly slower than aryliodides under standard Ullman conditions. In fact, it has been confirmed that the reaction of diphenylamine with 4-bromobiphenyl does not produce the desired arylamine even after many days under standard Ullman conditions. Accordingly, improved processes are desired for producing arylamines, such as N,N-diphenyl-4-aminobiphenyl, and similar compounds.

Figure 4:
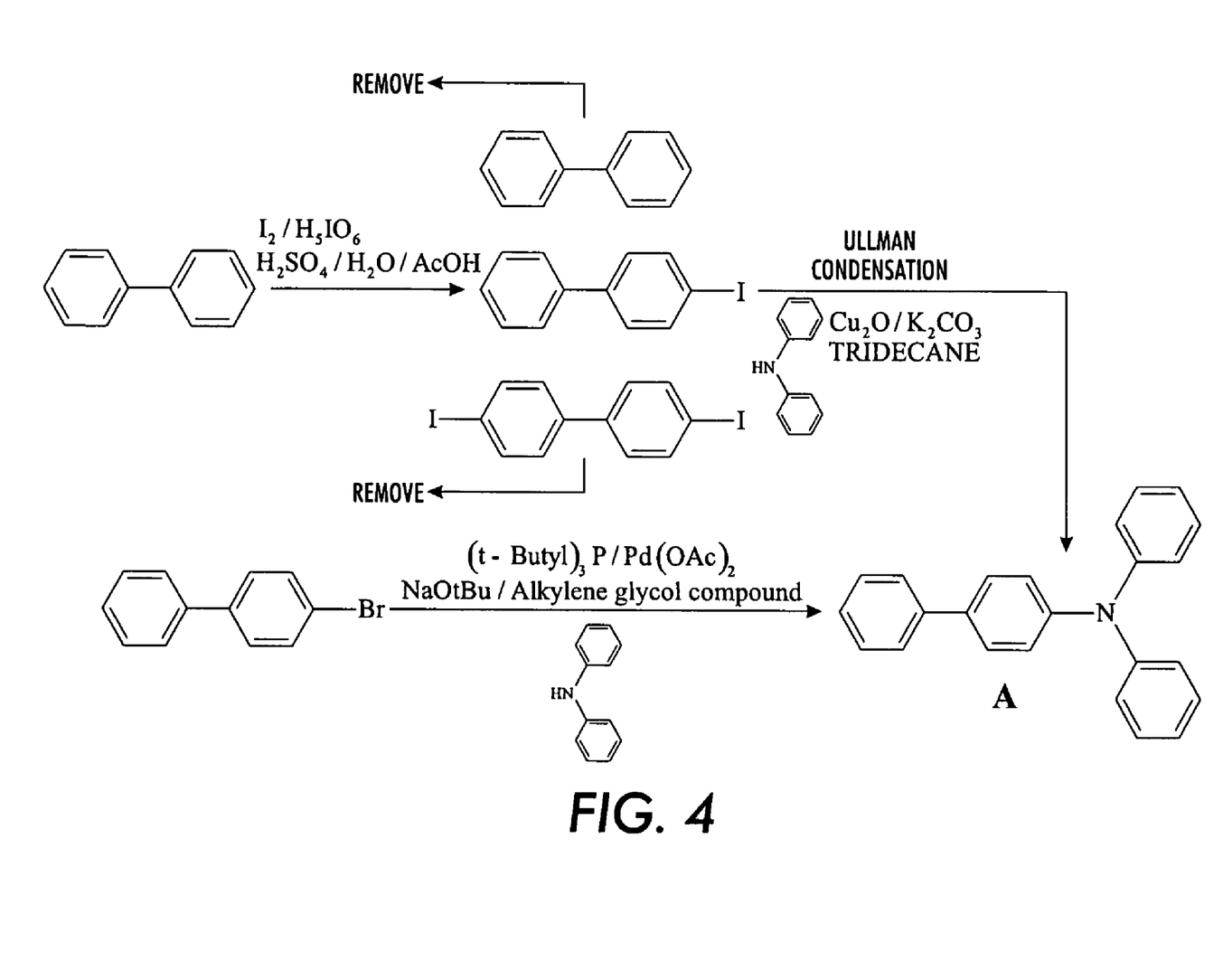
FIG. 4 sets forth two processes for the production of an arylamine derivative.

A process for producing this and other similar intermediate products is to react an arylhalide, such as an arylbromide, and an arylamine in the presence of a suitable catalyst. This process is shown alternatively in the reaction scheme of FIG. 4. For example, 4-bromobiphenyl and diphenylamine can be rapidly reacted to form N,N-diphenyl-4-aminobiphenyl using palladium acetate ligated with tri-t-butylphosphine as a catalyst and sodium t-butoxide base. This reaction proceeds rapidly, in about 1.5 hours, to produce the desired N,N-diphenyl-4-aminobiphenyl. This process is described in detail in commonly assigned, U.S. patent application Ser. No. 10/992,690 filed Nov. 22, 2004. Although this process uses a costly catalyst, such as a palladium catalyst, the cost of the catalyst is offset by the cost and time savings associated with the shorter and faster process and the cheapness of 4-bromobiphenyl.

An alternative or improved process is now described in detail.

According to embodiments, an arylhalide such as an arylbromide and an arylamine are used as starting materials. Any suitable arylhalide can be used, such as arylbromides, arylchlorides, aryliodides, arylfluorides, and the like. Likewise, any suitable arylamine can be used. The selection of specific starting arylhalide and arylamine depend, for example, upon the desired final product. For example, in embodiments, the arylamine is an arylbromide such as 4-bromobiphenyl and the arylamine is diphenylamine, which react to form the arylamine N,N-diphenyl-4-aminobiphenyl.

In embodiments, where an arylbromide is used, the reaction, including the starting materials and final product, can generally be represented as follows:

Thus, in this embodiment, an arylbromide is reacted with a secondary arylamine to produce a tertiary arylamine.

In this reaction scheme, the arylbromide can be any suitable arylbromide, depending upon the desired final product. Thus, for example, in the above reaction scheme, the substituents $R^1$, $R^2$, $R^3$, $R^4$ and $R^5$, which can be the same or different, can be suitably selected to represent hydrogen, a halogen, an alkyl group having for example from 1 to about 20 carbon atoms (such as methyl, ethyl, propyl, butyl and the like), a hydrocarbon radical having for example from 1 to about 20 carbon atoms, an aryl group optionally substituted by one or more alkyl groups, an alkyl group containing a heteroatom such as oxygen, nitrogen, sulfur and the like having for example from 1 to about 20 carbon atoms, a hydrocarbon radical containing a heteroatom such as oxygen, nitrogen, sulfur and the like having for example from 1 to about 20 carbon atoms, an aryl group containing a heteroatom such as oxygen, nitrogen, sulfur and the like optionally substituted by one or more alkyl groups, and the like. In embodiments, one of $R^1$, $R^2$, $R^3$, $R^4$ and $R^5$, such as $R^3$, represents a phenyl group and the remaining represent H atoms. Thus, in this embodiment, the arylbromide is 4-bromobiphenyl.

Likewise, in this reaction scheme, the arylamine can be any suitable arylamine, depending upon the desired final product. Thus, for example, in the above reaction scheme, the substituents $R^6$, $R^7$, $R^8$, $R^9$, $R^{10}$, $R^{11}$, $R^{12}$, $R^{13}$, $R^{14}$, and $R^{15}$, which can be the same or different, can be suitably selected to represent hydrogen, a halogen, an alkyl group having for example from 1 to about 20 carbon atoms (such as methyl, ethyl, propyl, butyl and the like), a hydrocarbon radical having for example from 1 to about 20 carbon atoms, an aryl group optionally substituted by one or more alkyl groups, an alkyl group containing a heteroatom such as oxygen, nitrogen, sulfur and the like having for example from 1 to about 20 carbon atoms, a hydrocarbon radical containing a heteroatom such as oxygen, nitrogen, sulfur and the like having for example from 1 to about 20 carbon atoms, an aryl group containing a heteroatom such as oxygen, nitrogen, sulfur and the like optionally substituted by one or more alkyl groups, and the like. In embodiments, each of $R^6$, $R^7$, $R^8$, $R^9$, $R^{10}$, $R^{11}$, $R^{12}$, $R^{13}$, $R^{14}$, and $R^{15}$ represent H atoms. Thus, in certain embodiments, the arylamine is diphenylamine.

The reactants are reacted in the presence of a suitable catalyst. Although not particularly limited, suitable catalysts are those that are known or discovered to be useful for formation of nitrogen-carbon bonds. For example, suitable catalysts include palladium ligated catalysts, such as those disclosed by Buchwald et al. and Hartwig et al. (for example in Michele C. HARRIS et al; "One-Pot Synthesis of Unsymmetrical Triarylamines from Aniline Precursors"; J. Org. Chem. Vol. 65, pp. 5327-5333 (2000), the disclosure of which is totally incorporated herein by reference).

In embodiments, a particular suitable catalyst is a palladium acetate ligated with tri-t-butylphosphine and sodium t-butoxide base. However, it will be apparent that other ligands, such as tri- or di-substituted phosphine ligands, could also be used to produce suitable results (from the point of view of conversion and yield), and thus would be suitable to ligate palladium or other metals and thus act to catalyze the process described in this disclosure. It will also be apparent that the use of phosphine-type ligands to ligate palladium are not the only ligate options, and other ligates are known or may become known to allow palladium to have catalytic activity under the described conditions. For example, nitrogen, oxygen or other heteroatom containing organic compounds as well as halogens are known to ligate to palladium.

The reaction is carried out in the presence of the catalyst, and can be conducted in batch or continuous mode. However, in embodiments, the reaction is conducted in batch mode. For example, the reaction can be carried out for a period of from about 30 minutes to about 5 hours or more, such as from about 30 minutes to about 10 or to about 15 hours, although a reaction time of from about 1 or from about 1.5 to about 2 or about 3 hours is suitable in embodiments.

The reaction is carried out in a suitable solvent or solvent mixture, comprising an alkylene glycol compound. When a solvent mixture is used, the solvent mixture can comprise an alkylene glycol compound and a suitable organic co-solvent such as hydrocarbons, ethers and the like. Mixtures of alkylene glycol compounds and organic solvents can be chosen, for example, to help produce a two-phase mixture on workup of the reaction. The alkylene glycol compound therefore enables subsequent separation and re-use of the palladium catalyst, thus providing cost reductions in the arylamine synthesis process.

Any suitable alkylene glycol compound, including unsubstituted alkylene glycol or substituted alkylene glycol and their derivatives, can be used as the reaction solvent. The alkylene glycol compound can have any suitable alkyl chain length, such as from 1 to about 20 or more carbon atoms such as methyl, ethyl, propyl, butyl, and the like. Thus, suitable alkylene glycol compounds can include methylene glycol, ethylene glycol, propylene glycol, 1,4-butylene glycol, and the like. The alkylene glycol compound can also be in the form of oligomers or polymers, such as polyalkylene glycols such as polymethylene glycol, polyethylene glycol, polypropylene glycol, poly-(1,4-butylene) glycol, and the like. Furthermore, for example, the alkylene glycol compound can include any suitable ligand, or can be free of such ligands. Polyethylene glycol compounds, and their use as effective media for cross-coupling reactions, are disclosed in Jin-Heng Li et al., "Recyclable and Reusable Pd(OAc)$_2$/DABCO/PEG-400 System for Suzuki-Miyaura-Coupling Reaction," *Organic Letters*, Vol. 4, No. 25, pp. 4399-4401 (2002) and S. Chandrasekhar et al., "Polyethylene glycol (PEG) as a Resuable Solvent Medium for Organic Synthesis, Application in the Heck Reaction," *Journal of Organic Chemistry*, Vol. 70, pp. 5409-5412 (2005), the entire disclosures of which are incorporated herein by reference.

Accordingly, the term "alkylene glycol compound" refers, for example, to any of the conventional or developed alkylene glycols and polyalkylene glycols as described above. For example, the term "ethylene glycol compound" or more specifically "polyethylene glycol compound" refers to any of the conventional or developed polyethylene glycols, also known as homopolymers of ethylene oxide, and includes polyethylene glycol per se as well as those polyethylene glycol compounds as result from condensation polymerization of ethylene glycol and addition polymerization of ethylene oxide. The term "polyethylene glycol compound" thus encompasses those polymers having the repeating unit $(CH_2CH_2O)_n$, where n is selected to provide a compound having a desired molecular weight, such as where n is from about 5 to about 20,000 or from about 10 to about 10,000. For example, suitable polyethylene glycol compounds that can be used in the process include polyethylene glycol of the formula $HOCH_2(CH_2OCH_2)_nCH_2OH$ or $H(OCH_2CH_2)_nOH$, where n is selected to provide a compound having a desired molecular weight.

Other alkylene glycols that can be used include derivatives, such as derivatives commonly referred to as polyalkylene glycol mono-alkyl or bis-alkyl ethers where both alkyl groups can independently have, for example, from 1 to about 20 or to about 40 carbon atoms. Specific examples include polyethylene glycol dimethyl ether, polypropylene glycol dimethyl ether, polyethylene glycol methyl ether, polyproplene glycol methyl ether, polyethylene glycol lauryl alcohol ether, polyproplene glycol lauryl alcohol ether, polyethylene glycol oleyl alcohol ether, polypropylene glycol oleyl alcohol ether; polyalkylene glycol aryl ethers such as polyethylene glycol aryl ethers; polyalkylene glycol esters such as polyethylene glycol esters; polyalkylene glycol ethers of acetylene diols such as polyethylene glycol ethers of acetylene diols; mixed polyalkylene glycol condensates such as polyethylene glycol/polypropylene glycol condensates; and the like.

In embodiments, it is preferred that the alkylene glycol compound has a weight average molecular weight of from about 100 to about 1,000,000. For example, the alkylene glycol compound can have a weight average molecular weight of from about 100 or from about 800 to about 1,000 or to about 10,000, such as from about 600 to about 2,000.

Further, in embodiments, the alkylene glycol compound is desirably liquid at room temperature (about 20° C. to about 25° C.), or is solid at room temperature but melts in a range between room temperature and the temperature at which the described process is conducted. Alternatively, suitable alkylene glycol compounds can also be solids at room temperature, but in the presence of either organic solvents or water have a melting point that is depressed to be between room temperature and the temperature at which the described process is conducted. Accordingly, in embodiments, suitable alkylene glycol compounds include those that are or become liquid at temperatures ranging from about room temperature to a reaction temperature. Typical reaction temperatures can be, for example, from about 30 to about 150° C. or more, such as from about 50 to about 125° C. or from about 75 to about 100° C. However, other reaction temperatures can be used, in embodiments.

In embodiments, the alkylene glycol compound can be used in combination with one or more conventional suitable solvent, such as an organic solvent. Suitable organic co-solvents include hexane, ether, toluene, decane, other hydrocarbon solvents (either aromatic or saturated hydrocarbons), other ethers such as tetrahydrofuran, dimethoxyethane, and alcohols such as butanol, hexanol and the like and mixtures thereof.

The choice of specific alkylene glycol compound and optional co-solvent can be decided based on the solubility of the starting materials, intermediates and final products, and will be readily apparent or within routine experimentation to those skilled in the art. For example, it is desired in embodiments that the starting materials such as the arylhalide, arylamine and catalyst are soluble in the alkylene glycol compound and optional co-solvent, while the formed arylamine product is soluble in an organic solvent but is insoluble in the alkylene glycol compound, and the catalyst remains soluble in the alkylene glycol compound after completion of the reaction. In embodiments, "soluble" refers to, for example, the specified material being substantially soluble in the respective solvent, although complete (100%) solubility is not necessarily required. Likewise, in embodiments, "insoluble" refers to, for example, the specified material being substantially insoluble in the respective solvent, although complete (100%) insolubility is not necessarily required. Furthermore the choice of alkylene glycol compound and optional co-solvent can be decided based on the desired operating temperature range. In some embodiments, the described process may be exothermic and precautions should be taken to ensure that a mixture of alkylene glycol compound and a suitable organic co-solvent is chosen that is capable of dispersing the produced heat by, for example, refluxing and cooling at such a rate so as to control the exotherm. In embodiments, a mixture of alkylene glycol compound and a co-solvent can be used, as the co-solvent will typically reflux whereas the alkylene glycol compound will not. The reaction should be conducted under an atmosphere of inert gas (such as nitrogen or argon) so as to preclude deactivation of catalyst or base by oxygen or atmospheric moisture.

After the reaction is completed, suitable separation, filtration, and/or purification processes can be conducted, as desired to a desired purity level. For example, the desired arylamine product can be subjected to conventional organic washing steps, can be separated, can be decolorized (if necessary), treated with known absorbents (such as silica, alumina and clays, if necessary) and the like. The final product can be isolated, for example, by a suitable extraction and/or recrystallization procedure. The final product can also be dried, for example, by air drying, vacuum drying, or the like. All of these procedures are conventional and will be apparent to those skilled in the art.

However, a particular benefit of embodiments is that the desired final product and the palladium catalyst can be easily separated, such that the catalyst can be recycled and re-used. A benefit of the alkylene glycol compound is that, once the reaction is complete, the desired arylamine product can be separated from the catalyst and alkylene glycol compound by extraction, such as by the addition of cyclohexane, linear alkanes (such as having an alkyl group of from 1 to about 20 or to about 40 carbon atoms), mixtures thereof, and the like. Addition of the cyclohexane causes the formation of a multi-phase medium such as a two-phase. In this multi-phase medium, one phase (such as the upper organic phase) includes the desired arylamine final product; and one phase (such as the lower alkylene glycol compound phase) includes the palladium catalyst. These phases can be easily separated, so that the desired arylamine product can be isolated, and the catalyst-carrying alkylene glycol compound phase can be re-used in a subsequent process. For example, the catalyst-carrying alkylene glycol compound phase can be first isolated and purified, such as by drying, or it can be directly recharged with additional reactants to conduct a further arylamine synthesis reaction. In embodiments, the relative amounts and proportions of the phases in the multi-phase medium may vary, depending upon, for example, the specific starting materials, intermediates and final products, the specific alkylene glycol compound, optional co-solvent, and the like.

Accordingly, in embodiments, the synthesis method further comprises adding sufficient amounts of organic solvent such as cyclohexane to provide a multi-phase medium.

After the multi-phase medium is formed, at least the alkylene glycol compound phase is removed for subsequent reuse of the entire alkylene glycol compound phase, or at least of the catalyst contained therein. For example, the process can be repeated a number of times, such as from 2 to about 20 or more, such as from 2 to about 10 times or 2 to about 5 times, without loss of catalytic activity. However, it has been found that catalytic activity may decrease as a function of the number of times of re-use. If desired, and as appropriate, the remaining phases, including the upper organic phase including the arylamine product, can also be separated, and appropriately processed.

In embodiments, any suitable ratios of arylhalide, arylamine, catalyst, and alkylene glycol compound can be used. For example, in one embodiment, the ratio of arylamine to arylhalide can be about 1:1 to about 2:1, such as from about 1:1 to about 1.5:1 or from about 1.05:1 to about 1.2:1. The catalyst can be used in embodiments in an amount of from about 0.1 to about 20 mole % relative to the arylamine, such as from about 0.5 to about 10 mole %, or from about 1 to about 5 mole %. The alkylene glycol compound can be used in any suitable amount, such as an amount that provides an effective concentration for the reaction. For example, in embodiments, the alkylene glycol compound can be used in an amount to provide an effective concentration of reaction of from about 5 to about 50 weight %, such as from about 8 to about 40 weight % or from about 10 to about 30 weight %.

The arylamine produced by this process can itself be used as a final product, or it can be further processed and/or reacted to provide other compounds for their separate use. For example, the arylamine can be used itself as a charge transport material in an electrostatographic imaging member, or it can be further processed and/or reacted to provide other charge transport materials or other compounds useful in such electrostatographic imaging member. An exemplary electrostatographic imaging member will now be described in greater detail.

In electrophotographic photoreceptors of embodiments, the photoreceptors can include various layers such as undercoating layers, charge generating layers, charge transport layers, overcoat layers, and the like. The overcoating layers of embodiments can be a silicon overcoat layer, which can comprise one or more silicon compounds, a resin, and a charge transport molecule such as an arylamine.

In embodiments, the resin may be a resin soluble in a liquid component in a coating solution used for formation of a silicon overcoat layer. Such a resin soluble in the liquid component may be selected based upon the kind of liquid component. For example, if the coating solution contains an alcoholic solvent (such as methanol, ethanol or butanol), a polyvinyl acetal resin such as a polyvinyl butyral resin, a polyvinyl formal resin or a partially acetalized polyvinyl acetal resin in which butyral is partially modified with formal or acetoacetal, a polyamide resin, a cellulose resin such as ethyl cellulose and a phenol resin may be suitably chosen as the alcohol-soluble resins. These resins may be used either alone or as a combination of two or more resins. Of the above-mentioned resins, the polyvinyl acetal resin is particularly suitable in embodiments in terms of electric characteristics.

In embodiments, the weight-average molecular weight of the resin soluble in the liquid component may be from about 2,000 to about 1,000,000, such as from about 5,000 to about 50,000. When the average molecular weight is less than about 2,000, the effect of enhancing discharge gas resistance, mechanical strength, scratch resistance, particle dispersibility, etc., tends to become insufficient. However, when the average molecular weight exceeds about 1,000,000, the resin solubility in the coating solution decreases, and the amount of resin added to the coating solution may be limited and poor film formation in the production of the photosensitive layer may result.

Further, the amount of the resin soluble in the liquid component may be, in embodiments, from about 0.1 to about 15% by weight, or from about 0.5 to about 10% by weight, based on the total amount of the coating solution. When the amount added is less than 0.1% by weight, the effect of enhancing discharge gas resistance, mechanical strength, scratch resistance, particle dispersibility, etc. tends to become insufficient. However, if the amount of the resin soluble in the liquid component exceeds about 15% by weight, there is a tendency for formation of indistinct images when the electrophotographic photoreceptor of the disclosure is used at high temperature and high humidity.

In embodiments, for example, a "high temperature environment" or "high temperature conditions" refer to an atmosphere in which the temperature is at least about 28 to about 30° C. A "high humidity environment" or "high humidity conditions" refer to an atmosphere in which the relative humidity is at least about 75 to about 80%.

There is no particular limitation on the silicon compound used in embodiments of the disclosure, as long as it has at least one silicon atom. However, a compound having two or more silicon atoms in its molecule may be used in embodiments. The use of the compound having two or more silicon atoms in its molecule allows both the strength and image quality of the electrophotographic photoreceptor to be achieved at higher levels.

Further, in embodiments, the silicon compounds may include silane coupling agents such as a tetrafunctional alkoxysilane such as tetramethoxysilane or tetraethoxysilane; a trifunctional alkoxysilane such as methyltrimethoxysilane, methyltriethoxysilane, ethyltrimethoxysilane, methyltrimethoxyethoxysilane, vinyltrimethoxysilane, vinyltriethoxysilane, phenyltrimethoxysilane, γ-glycidoxypropylmethyldiethoxysilane, γ-glycidoxypropyltrimethoxysilane, γ-glycidoxypropyltriethoxysilane, γ-aminopropyltriethoxysilane, γ-aminopropyltrimethoxysilane, γ-aminopropylmethyldimethoxysilane, N-β-(aminoethyl)-γ-aminopropyltriethoxysilane, (tridecafluoro-1,1,2,2-tetrahydrooctyl)triethoxysilane, (3,3,3-trifluoropropyl)trimethoxysilane, 3-(heptafluoroisopropoxy)propyltriethoxysilane, 1H,1H,2H,2H-perfluoroalkyltriethoxysilane, 1H,1H,2H,2H-perfluorodecyltriethoxysilane or 1H,1H,2H,2H-perfluorooctyltriethoxysilane; a bifunctional alkoxysilane such as dimethyldimethoxysilane, diphenyldimethoxysilane or methylphenyldimethoxysilane; and a monofunctional alkoxysilane such as trimethylmethoxysilane. In order to improve the strength of the photosensitive layer, trifunctional alkoxysilanes and tetrafunctional alkoxysilanes may be used in embodiments, and in order to improve the flexibility and film forming properties, monofunctional alkoxysilanes and bifunctional alkoxysilanes may be used in embodiments.

Silicone hard coating agents containing these coupling agents can also be used in embodiments. Commercially available hard coating agents include KP-85, X-40-9740 and X-40-2239 (available from Shinetsu Silicone Co., Ltd.), and AY42-440, AY42-441 and AY49-208 (available from Toray Dow Corning Co., Ltd.).

In order to further improve the stain adhesion resistance and lubricity of embodiments of the electrophotographic photoreceptor, various fine particles can also be added to the silicon compound-containing layer. The fine particles may be used either alone or as a combination of two or more such fine particles. Non-limiting examples of the fine particles include fine particles containing silicon, such as fine particles containing silicon as a constituent element, and specifically include colloidal silica and fine silicone particles.

Colloidal silica used in embodiments as the fine particles containing silicon in the disclosure is selected from an acidic or alkaline aqueous dispersion of the fine particles having an average particle size of 1 to 100 nm, or 10 to 30 nm, and a dispersion of the fine particles in an organic solvent such as an alcohol, a ketone or an ester, and generally, commercially available particles can be used.

There is no particular limitation on the solid content of colloidal silica in a top surface layer of the electrophotographic photoreceptor of embodiments. However, in embodiments, colloidal silica is used within the range of from about 1 to about 50% by weight, such as from about 5 to about 30% by weight, based on the total solid content of the top surface layer, in terms of film forming properties, electric characteristics and strength.

The fine silicone particles used as the fine particles containing silicon in the disclosure are selected from silicone resin particles, silicone rubber particles and silica particles surface-treated with silicone, which are spherical and have an average particle size of from about 1 to 500 nm, such as from about 10 to about 100 nm, and generally, commercially available particles can be used in embodiments.

In embodiments, the fine silicone particles are small-sized particles that are chemically inactive and excellent in dispersibility in a resin, and further are low in content as may be necessary for obtaining sufficient characteristics. Accordingly, the surface properties of the electrophotographic photoreceptor can be improved without inhibition of the crosslinking reaction. That is to say, fine silicone particles improve the lubricity and water repellency of surfaces of electrophotographic photoreceptors where incorporated into strong crosslinked structures, which may then be able to maintain good wear resistance and stain adhesion resistance for a long period of time. The content of the fine silicone particles in the silicon compound-containing layer of embodiments may be within the range of from about 0.1 to about 20% by weight, such as from about 0.5 to about 10% by weight, based on the total solid content of the silicon compound-containing layer.

Other fine particles that may be used in embodiments include fine fluorine-based particles such as ethylene tetrafluoride, ethylene trifluoride, propylene hexafluoride, vinyl fluoride and vinylidene fluoride, and semiconductive metal oxides such as $ZnO$—$Al_2O_3$, $SnO_2$—$Sb_2O_3$, $In_2O_3$—$SnO_2$, $ZnO$—$TiO_2$, $MgO$—$Al_2O_3$, $FeO$—$TiO_2$, $TiO_2$, $SnO_2$, $In_2O_3$, $ZnO$ and $MgO$.

In conventional electrophotographic photoreceptors, when the above-mentioned fine particles are contained in the photosensitive layer, the compatibility of the fine particles with a charge transport substance or a binding resin may become insufficient, which causes layer separation in the photosensitive layer, and thus the formation of an opaque film. As a result, the electric characteristics have deteriorated in some cases. In contrast, the silicon compound-containing layer of embodiments (a charge transport layer in this case) may contain the resin soluble in the liquid component in the coating solution used for formation of this layer and the silicon compound, thereby improving the dispersibility of the fine particles in the silicon compound-containing layer. Accordingly, the pot life of the coating solution can be sufficiently prolonged, and it becomes possible to prevent deterioration of the electric characteristics.

Further, an additive such as a plasticizer, a surface modifier, an antioxidant, or an agent for preventing deterioration by light can also be used in the silicon compound-containing layer of embodiments. Non-limiting examples of plasticizers that may be used in embodiments include, for example, biphenyl, biphenyl chloride, terphenyl, dibutyl phthalate, diethylene glycol phthalate, dioctyl phthalate, triphenylphosphoric acid, methylnaphthalene, benzophenone, chlorinated paraffin, polypropylene, polystyrene and various fluorohydrocarbons.

The antioxidants may include an antioxidant having a hindered phenol, hindered amine, thioether or phosphite partial structure. This is effective for improvement of potential stability and image quality in environmental variation. The antioxidants include an antioxidant having a hindered phenol, hindered amine, thioether or phosphite partial structure. This is effective for improvement of potential stability and image quality in environmental variation. For example, the hindered phenol antioxidants include Sumilizer BHT-R, Sumilizer MDP-S, Sumilizer BBM-S, Sumilizer WX-R, Sumilizer NW, Sumilizer BP-76, Sumilizer BP-101, Sumilizer GA-80, Sumilizer GM and Sumilizer GS (the above are manufactured by Sumitomo Chemical Co., Ltd.), IRGANOX 1010, IRGANOX 1035, IRGANOX 1076, IRGANOX 1098, IRGANOX 1135, IRGANOX 1141, IRGANOX 1222, IRGANOX 1330, IRGANOX 1425WLj, IRGANOX 1520Lj, IRGANOX 245, IRGANOX 259, IRGANOX 3114, IRGANOX 3790, IRGANOX 5057 and IRGANOX 565 (the above are manufactured by Ciba Specialty Chemicals), and Adecastab AO-20, Adecastab AO-30, Adecastab AO-40, Adecastab AO-50, Adecastab AO-60, Adecastab AO-70, Adecastab AO-80 and Adecastab AO-330i (the above are manufactured by Asahi Denka Co., Ltd.). The hindered amine antioxidants include Sanol LS2626, Sanol LS765, Sanol LS770, Sanol LS744, Tinuvin 144, Tinuvin 622LD, Mark LA57, Mark LA67, Mark LA62, Mark LA68, Mark LA63 and Sumilizer TPS, and the phosphite antioxidants include Mark 2112, Mark PEP•8, Mark PEP•24G, Mark PEP•36, Mark 329K and Mark HP•10. Of these, the hindered phenol and hindered amine antioxidants are particularly suitable, in embodiments.

There is no particular limitation on the thickness of the silicon-containing layer, however, in embodiments, the silicon-containing layer may be in the range from about 2 to about 5 μm in thickness, such as from about 2.7 to about 3.2 μm in thickness.

The electrophotographic photoreceptor of embodiments may be either a function-separation-type photoreceptor, in which a layer containing a charge generation substance (charge generation layer) and a layer containing a charge transport substance (charge transport layer) are separately provided, or a monolayer-type photoreceptor, in which both the charge generation layer and the charge transport layer are contained in the same layer, as long as the electrophotographic photoreceptor of the particular embodiment has the photosensitive layer provided with the above-mentioned silicon compound-containing layer. The electrophotographic photoreceptor will be described in greater detail below, taking the function-separation-type photoreceptor as an example.

Figure 1:
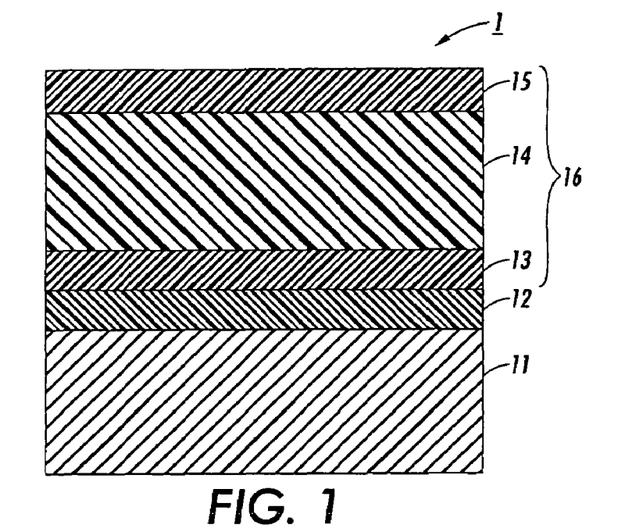
FIG. 1 is a schematic cross sectional view showing an embodiment of an electrophotographic photoreceptor of the disclosure.

FIG. 1 is a cross-sectional view schematically showing an embodiment of the electrophotographic photoreceptor of the disclosure. The electrophotographic photoreceptor 1 shown in FIG. 1 is a function-separation-type photoreceptor in which a charge generation layer 13 and a charge transport layer 14 are separately provided. That is, an underlayer 12, the charge generation layer 13, the charge transport layer 14 and a protective layer 15 are laminated onto a conductive support 11 to form a photosensitive layer 16. The protective layer 15 contains a resin soluble in the liquid component contained in the coating solution used for formation of this layer and the silicon compound. The various layers of the photoreceptor shown in FIG. 1 are generally known, and are described in detail in the above-mentioned commonly owned and copending applications, the entire disclosures of which are incorporated herein by reference.

The electrophotographic photoreceptor of embodiments should not be construed as being limited to the above-mentioned constitution. For example the electrophotographic photoreceptor shown in FIG. 1 is provided with the protective layer 15. However, when the charge transport layer 14 contains the resin soluble in the liquid component in the coating solution used for formation of this layer and the silicon compound, the charge transport layer 14 may be used as a top surface layer (a layer on the side farthest apart from the support 11) without using the protective layer 15. In this case, the charge transport substance contained in the charge transport layer 14 is desirably soluble in the liquid component in the coating solution used for formation of the charge transport layer 14. For example, when the coating solution used for formation of the charge transport layer 14 contains an alcohol solvent, the silicon compounds described above, such as compounds represented by the following formulas, can be used as the charge transport substances.

-continued

Figure 3:
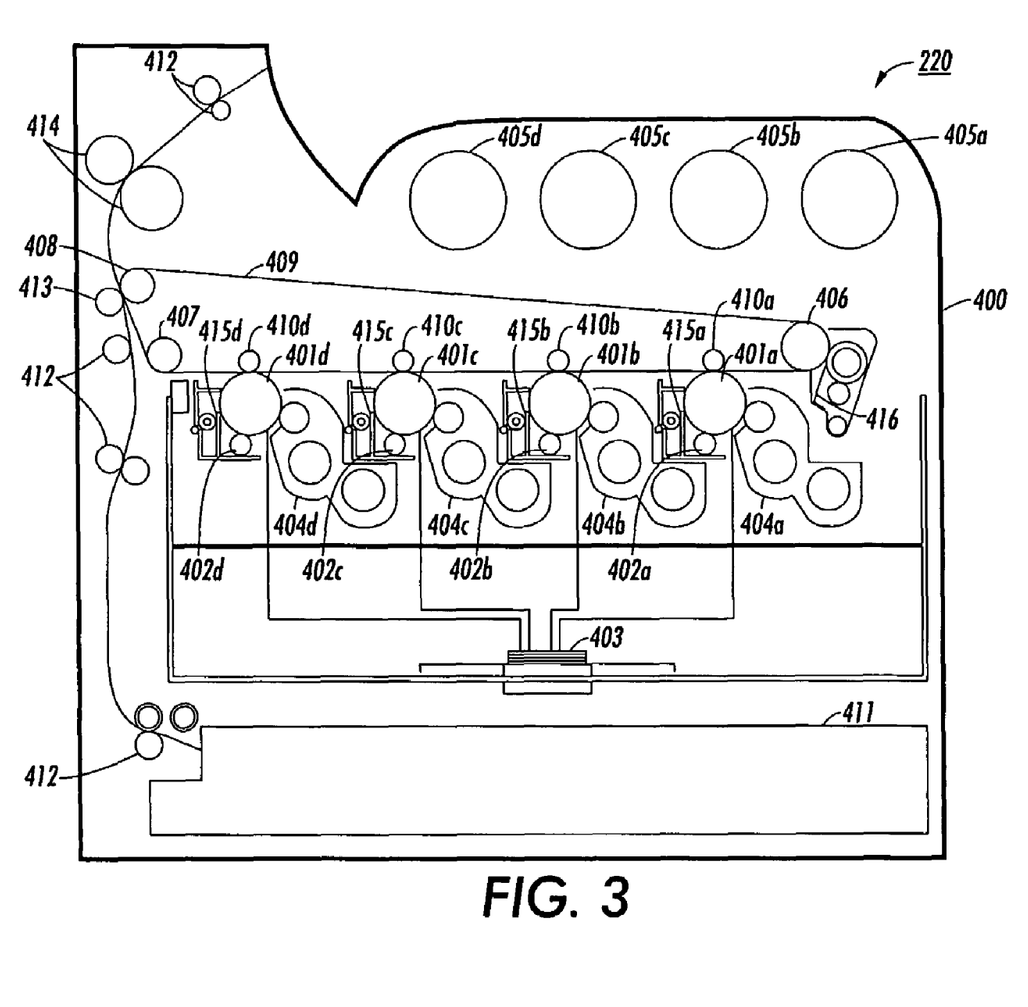
FIG. 3 is a schematic view showing another embodiment of an image forming apparatus of the disclosure.

In embodiments, a particularly suitable charge transport molecule is the following arylamine (Compound C—FIG. 5):

FIG. 3 is a cross-sectional view showing another exemplary embodiment of an image forming apparatus. The image forming apparatus 220 shown in FIG. 3 is an image forming apparatus of an intermediate transfer system, and four electrophotographic photoreceptors 401a to 401d are arranged in parallel with each other along an intermediate transfer belt 409 in a housing 400.

Here, the electrophotographic photoreceptors 401a to 401d carried by the image forming apparatus 220 are each the electrophotographic photoreceptors. Each of the electrophotographic photoreceptors 401a to 401d may rotate in a predetermined direction (counterclockwise on the sheet of FIG. 3), and charging rolls 402a to 402d, developing device 404a to 404d, primary transfer rolls 410a to 410d and cleaning blades 415a to 415d are each arranged along the rotational direction thereof. In each of the developing device 404a to 404d, four-color toners of yellow (Y), magenta (M), cyan (C) and black (B) contained in toner cartridges 405a to 405d can be supplied, and the primary transfer rolls 410a to 410d are each brought into abutting contact with the electrophotographic photoreceptors 401a to 401d through an intermediate transfer belt 409.

Further, a laser light source (exposure unit) 403 is arranged at a specified position in the housing 400, and it is possible to irradiate surfaces of the electrophotographic photoreceptors 401a to 401d after charging with laser light emitted from the laser light source 403. This performs the respective steps of charging, exposure, development, primary transfer and cleaning in turn in the rotation step of the electrophotographic photoreceptors 401a to 401d, and toner images of the respective colors are transferred onto the intermediate transfer belt 409, one over the other.

The intermediate transfer belt 409 is supported with a driving roll 406, a backup roll 408 and a tension roll 407 at a specified tension, and rotatable by the rotation of these rolls without the occurrence of deflection. Further, a secondary transfer roll 413 is arranged so that it is brought into abutting contact with the backup roll 408 through the intermediate transfer belt 409. The intermediate transfer belt 409 which has passed between the backup roll 408 and the secondary transfer roll 413 is cleaned up by a cleaning blade 416, and then repeatedly subjected to the subsequent image formation process.

Further, a tray (tray for a medium to which a toner image is to be transferred) 411 is provided at a specified position in the housing 400. The medium to which the toner image is to be transferred (such as paper) in the tray 411 is conveyed in turn between the intermediate transfer belt 409 and the secondary transfer roll 413, and further between two fixing rolls 414 brought into abutting contact with each other, with a conveying roll 412, and then delivered out of the housing 400.

According to the exemplary image forming apparatus 220 shown in FIG. 3, the use of electrophotographic photoreceptors of embodiments as electrophotographic photoreceptors 401a to 401d may achieve discharge gas resistance, mechanical strength, scratch resistance, etc. on a sufficiently high level in the image formation process of each of the electrophotographic photoreceptors 401a to 401d. Accordingly, even when the photoreceptors are used together with the contact charging devices or the cleaning blades, or further with the spherical toner obtained by chemical polymerization, good image quality can be obtained without the occurrence of image defects such as fogging. Therefore, also according to the image forming apparatus for color image formation using the intermediate transfer body, such as this embodiment, the image forming apparatus which can stably provide good image quality for a long period of time is realized.

Figure 2:
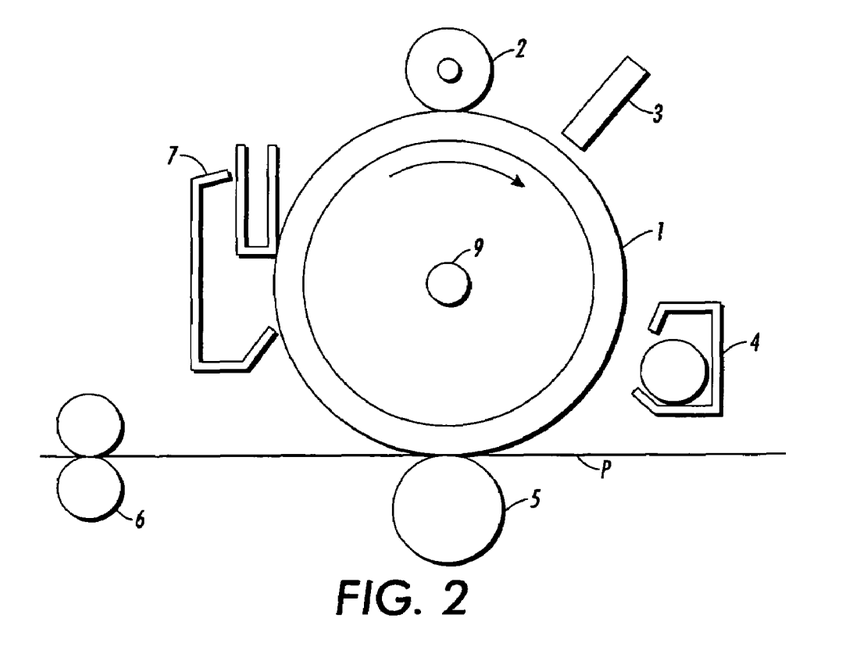
FIG. 2 is a schematic view showing an embodiment of an image forming apparatus of the disclosure.

The disclosure should not be construed as being limited to the above-mentioned embodiments. For example, each apparatus shown in FIG. 2 or 3 may be equipped with a process cartridge comprising the electrophotographic photoreceptor 1 (or the electrophotographic photoreceptors 401a to 401d) and charging device 2 (or the charging devices 402a to 402d). The use of such a process cartridge allows maintenance to be performed more simply and easily.

Further, in embodiments, when a charging device of the non-contact charging system such as a corotron charger is used in place of the contact charging device 2 (or the contact charging devices 402a to 402d), sufficiently good image quality can be obtained.

An example is set forth hereinbelow and is illustrative of different compositions and conditions that can be utilized in practicing the disclosure. All proportions are by weight unless otherwise indicated. It will be apparent, however, that the disclosure can be practiced with many types of compositions and can have many different uses in accordance with the disclosure above and as pointed out hereinafter.

EXAMPLES

Example 1

Preparation of Arylamine Intermediate in Polyethylene Glycol Compound

To a 500 mL flask fitted with mechanical stirrer, argon inlet and reflux condenser is charged palladium(II)acetate (0.47 g, 0.01 mol %) and tri-t-butylphosphine stock solution (0.46 mL 2.7 mmol) and dissolved in 75 mL toluene. The solution is stirred for 1 hour to allow for dissolution of palladium acetate. Then sequentially, 75 mL of polyethylene glycol diemthyl ether, 4-bromobiphenyl (50 g, 224 mmol), diphenylamine (39.7 g, 235 mmol), and sodium t-butoxide (38.7 g, 403 mmol) are added with stirring. The reaction is heated to 90° C. over a 30 min period. An exotherm is observed and the heating is shut off. After 2 hours the reaction is complete and HPLC analysis confirms 99% conversion of diphenylamine to N-biphenyl-diphenylamine.

Following completion of the reaction, the reaction mixture is cooled to room temperature (about 20° C. to about 25° C.), and cyclohexane is added to produce a two-phase medium. The top organic layer is removed, and is treated with Filtrol-24 and $Al_2O_3$ at 65° C. for 2 hours. The absorbents are filtered while the solution is hot. The cyclohexane solution is concentrated and isopropanol is added followed by methanol to complete precipitation of N-biphenyl-diphenylamine. The solid N-biphenyl-diphenylamine is filtered and washed with methanol, air dried then finally vacuum dried (60° C./5 mmHg) overnight. Ashing followed by ICP analysis does not detect any residual palladium present.

The lower polyethylene glycol dimethyl ether phase is collected and dried. The reaction is repeated again with re-charging of the reactants, as described above. The process proceeds in the same manner, with the same results, indicating that the palladium catalyst is recycled. The process is repeated five times without any loss of catalytic activity.

Comparative Example 1

Preparation of Arylamine Intermediate in an Organic Solvent

To a 2 L flask fitted with mechanical stirrer, argon inlet and reflux condenser is charged palladium(II)acetate (1.57 g, 5 mol %) and 226 mL of tri-t-butylphosphine stock solution (5 g tri-t-butylphosphine in 1 L toluene). The solution is stirred for 1 hour to allow for dissolution of palladium acetate. Then sequentially, 4-bromobiphenyl (164 g, 1.0 equiv), diphenylamine (130 g, 1.05 equiv), toluene (410 mL) and sodium t-butoxide (127 g) are added with stirring. The reaction is heated to 70° C. over a 30 min period. A large exotherm is observed and the heating is shut off. After 1 hr 15 min the exotherm subsides and HPLC analysis confirms complete conversion of diphenylamine to N-biphenyl-diphenylamine.

Following completion of the reaction, toluene (200 mL) is added and the solution is filtered to remove insoluble materials. The solids are washed with toluene so as to have a final liqueur with a volume of 2 L. This solution is treated with Filtrol-24 (40 g) and $Al_2O_3$ (40 g) at 90° C. for 2 hours. The absorbents are filtered while the solution is hot. A second treatment with $Al_2O_3$ (8 g) at 90° C. is necessary to completely remove color (most likely residual palladium catalyst). The toluene solution is concentrated to 400 mL and isopropanol (500 mL) is added followed by methanol (750 mL) to complete precipitation of N-biphenyl-diphenylamine. The solid N-biphenyl-diphenylamine is filtered and washed with methanol (250 mL), air dried then finally vacuum dried (60° C./5 mmHg) overnight. The final yield of N-biphenyl-diphenylamine is 214.85 g (95.1%). HPLC, 1H NMR and elemental analysis confirm purity of N-biphenyl-diphenylamine at >99.5%. Ashing followed by ICP analysis does not detect any residual palladium present and is presumed to be removed by absorption to either the $Al_2O_3$ or the Filtrol-24 or both.

It will be appreciated that various of the above-disclosed and other features and functions, or alternatives thereof, may be desirably combined into many other different systems or applications. Also that various presently unforeseen or unanticipated alternatives, modifications, variation or improvements therein may be subsequently made by those skilled in the art which are also intended to be encompassed by the following claims.

What is claimed is:

1. A process for the preparation of a tertiary arylamine compound, comprising reacting an arylhalide and an arylamine in the presence of an alkylene glycol compound and a catalyst, wherein the catalyst comprises a palladium acetate ligated with a group selected from the group consisting of phosphine groups and heteroatom containing organic groups.

2. The process according to claim 1, wherein the alkylene glycol compound is a solvent for the arylhalide and the arylamine.

3. The process according to claim 1, wherein the alkylene glycol compound is a monomer or polymer of an alkylene glycol comprising an alkyl group of from 1 to about 20 carbon atoms.

4. The process according to claim 1, wherein the alkylene glycol compound is a polyethylene glycol compound comprising a repeating unit $(CH_2CH_2O)_n$, where n is from about 5 to about 20,000.

5. The process according to claim 1, wherein the alkylene glycol compound is a polyalkylene glycol mono-alkyl ether or a polyalkylene glycol bis-alkyl ether.

6. The process according to claim 1, wherein the alkylene glycol compound is a polyethylene glycol compound selected from the group consisting of polyethylene glycol alkyl ethers, polyethylene glycol aryl ethers, polyethylene glycol esters, polyethylene glycol ethers of acetylene diols, polyethylene glycol/polypropylene glycol condensates, and mixtures thereof.

7. The process according to claim 1, wherein the alkylene glycol compound is a polyethylene glycol alkyl ether selected from the group consisting of polyethylene glycol dimethyl ether, polyethylene glycol methyl ether, polyethylene glycol lauryl alcohol ether, and polyethylene glycol oleyl alcohol ether.

8. The process according to claim 1, wherein the alkylene glycol compound has a weight average molecular weight of from about 100 to about 1,000,000.

9. The process according to claim 1, wherein the alkylene glycol compound is liquid at room temperature, is solid at room temperature but liquid at a reaction temperature, or is solid at room temperature but liquid at reaction temperature when mixed with water or an organic solvent.

10. The process according to claim 1, wherein the catalyst comprises a palladium acetate ligated with tri-t-butylphosphine and sodium t-butoxide base.

11. The process according to claim 1, further comprising adding an organic solvent to a product formed by the reaction.

12. The process according to claim 11, wherein the addition forms a multi-phase system comprising a first phase comprising the tertiary arylamine and the organic solvent, and a second phase comprising the catalyst and the alkylene glycol compound.

13. The process according to claim 12, further comprising separating said first phase and said second phase.

14. The process according to claim 1, wherein the arylhalide is an arylbromide and the arylamine is a secondary arylamine.

15. The process according to claim 14, wherein the arylbromide, secondary arylamine, and tertiary arylamine are represented as follows:

wherein:

R$^1$, R$^2$, R$^3$, R$^4$ and R$^5$, which can be the same or different, are selected from the group consisting of H, a halogen, an alkyl group, a hydrocarbon radical, an aryl group optionally substituted by one or more alkyl groups, an alkyl group containing a heteroatom, a hydrocarbon radical, and an aryl group containing a heteroatom and optionally substituted by one or more alkyl groups, and R$^6$, R$^7$, R$^8$, R$^9$, R$^{10}$, R$^{11}$, R$^{12}$, R$^{13}$, R$^{14}$, and R$^{15}$, which can be the same or different, are selected from the group consisting of H, a halogen, an alkyl group, a hydrocarbon radical, an aryl group optionally substituted by one or more alkyl groups, an alkyl group containing a heteroatom, a hydrocarbon radical containing a heteroatom, and an aryl group containing a heteroatom and optionally substituted by one or more alkyl groups.

16. The process according to claim 15, wherein the alkyl groups and hydrocarbon radicals, when present, independently have from 1 to about 20 carbon atoms.

17. The process according to claim 15, wherein at least one of R$^1$, R$^2$, R$^3$, R$^4$ and R$^5$ represents a phenyl group.

18. The process according to claim 15, wherein one of R$^1$, R$^2$, R$^3$, R$^4$ and R$^5$ represents a phenyl group and the rest of R$^1$, R$^2$, R$^3$, R$^4$ and R$^5$ represent hydrogen.

19. The process according to claim 17, wherein R$^3$ represents a phenyl group and the rest of R$^1$, R$^2$, R$^4$ and R$^5$ represent hydrogen.

20. The process according to claim 15, wherein each of R$^6$, R$^7$, R$^8$, R$^9$, R$^{10}$, R$^{11}$, R$^{12}$, R$^{13}$, R$^{14}$, and R$^{15}$ represent hydrogen.

21. The process according to claim 1, wherein the arylhalide is 4-bromobiphenyl, the arylamine is diphenylamine, and the tertiary arylamine compound is N,N-diphenyl-4-aminobiphenyl.

22. The process according to claim 1, wherein the process is accomplished in about 30 minutes to about 5 hours.

23. The process according to claim 1, wherein the process is conducted under an inert atmosphere.

24. The process according to claim 1, wherein a molar ratio of arylamine to arylhalide is from about 1:1 to about 2:1, the catalyst is present in an amount of from about 0.1 to about 20 mole % relative to the arylamine, and the alkylene glycol compound is present in an effective concentration of from about 5 to about 50 weight %.

25. A process for forming N,N-diphenyl-aminobiphenyl, comprising reacting bromobiphenyl and diphenylamine in a polyethylene glycol compound in the presence of a palladium catalyst, wherein the palladium catalyst comprises a palladium acetate ligated with a group selected from the group consisting of phosphine groups and heteroatom containing organic groups.

26. The process for claim 25, wherein the N,N-diphenyl-aminobiphenyl is N,N-diphenyl-4-aminobiphenyl, and the bromobiphenyl is 4-bromobiphenyl.

27. A process for forming a tertiary arylamine compound, comprising:

(a) forming a reaction medium comprising an arylbromide, an arylamine, an alkylene glycol compound, and a catalyst wherein the catalyst comprises a palladium acetate ligated with a group selected from the group consisting of phosphine groups and heteroatom containing organic groups;

(b) allowing said arylbromide and said arylamine to react in said reaction medium to form a reaction product;

(c) adding an organic solvent to the reaction product to form a multi-phase system comprising a first phase comprising the tertiary arylamine and the organic solvent, and a second phase comprising the catalyst and the alkylene glycol compound;

(d) separating said first phase from said second phase;

(e) adding additional arylbromide and arylamine to said second phase to form an additional reaction medium; and (f) repeating (b) to (d) at least one additional time to form additional arylamine compound.

* * * * *